US00PP09428P

United States Patent [19]

Jepsen

[11] Patent Number: Plant 9,428

[45] Date of Patent: Jan. 16, 1996

[54] KALANCHOË PLANT NAMED 'DEBBIE'

[75] Inventor: Knud Jepsen, Hinnerup, Denmark

[73] Assignee: Knud Jepsen A/S, Hinnerup, Denmark

[21] Appl. No.: 376,389

[22] Filed: Jan. 23, 1995

[51] Int. Cl.[6] ..... A01H 5/00

[52] U.S. Cl. ..... Plt./87.15

[58] Field of Search ..... Plt./87.15

*Primary Examiner*—James R. Feyrer

*Attorney, Agent, or Firm*—Foley & Lardner

[57] ABSTRACT

A new and distinct cultivar of Kalanchoë plant named 'Debbie' characterized by its excellent branching and bud production, small and narrow leaves, red petal color which at opening is 43A on topside and 43B on underside, natural compact growth habit and mother stock production of many uniform cuttings of good quality.

1 Drawing Sheet

The present invention relates to a new and distinct cultivar of Kalanchoë plant, botanically known as Kalanchoë, and referred to by the cultivar name 'Debbie'.

The new cultivar was referred to during the breeding and selection process by the designation No. 25/89-69, and is a product of a planned breeding program. The basic objective of the breeding program was to create a new Kalanchoë cultivar having smaller leaves, more buds, red flowers and rapid production time.

The new cultivar was originated from a cross made in a controlled breeding program in Hinnerup, Denmark. The female or seed parent was a cultivar designated 'Janni' and the male or pollen parent was a cultivar designated 'Rako'.

'Debbie' was discovered and selected by the inventor as a flowering plant within the progeny of the stated cross in a controlled environment in Hinnerup, Denmark.

Asexual reproduction of the new cultivar was first accomplished by the inventor in Hinnerup, Denmark in April 1989. Asexual reproduction of the new cultivar by stem cuttings, as performed by the inventor at Hinnerup, Denmark, has demonstrated that the combination of characteristics as herein disclosed for the new cultivar are firmly fixed and are retained through successive generations of asexual reproduction.

'Debbie' has not been observed under all possible environmental conditions. The phenotype may vary with variations in environment such as temperature, light intensity and day length without a change in the genotype of the plant. The following observations, measurements and values describe the new cultivar as grown in Hinnerup, Denmark under greenhouse conditions which closely approximate those generally used in commercial practice.

The following traits have been repeatedly observed and are determined to be basic characteristics of 'Debbie', which in combination, distinguish this Kalanchoë as a new and distinct cultivar:

1. Good number of buds.
2. Excellent branching.
3. Small and narrow leaves.
4. Rapid production time.
5. The mother stock gives many and uniform cuttings of good quality.
6. Naturally compact growth habit.
7. Good keeping quality.

The new cultivar is most similar to 'Rako'. 'Debbie' is principally distinguished from 'Rako' by its better branching, faster production time, and a larger number of cuttings per plant.

The accompanying photographic drawings show a typical specimen plant of the new cultivar. The colors appearing in the photograph are as true as possible with color illustrations of this type.

Figure 1:
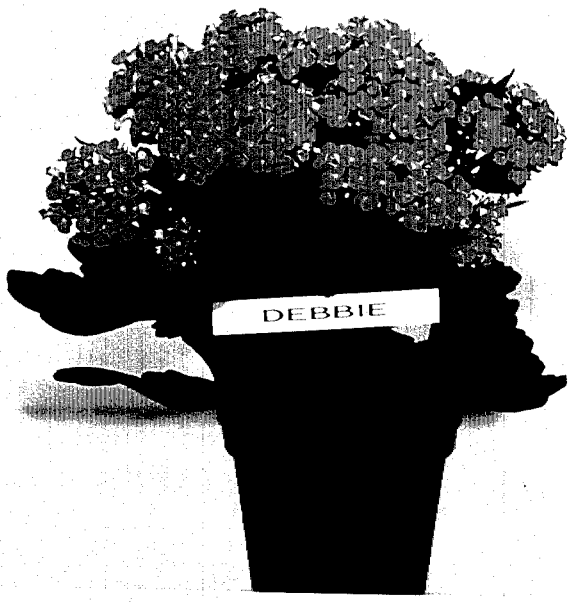
FIG. 1 is a sideview of 'Debbie' showing the excellent branching and profuse flowering of the plant.
Figure 2:
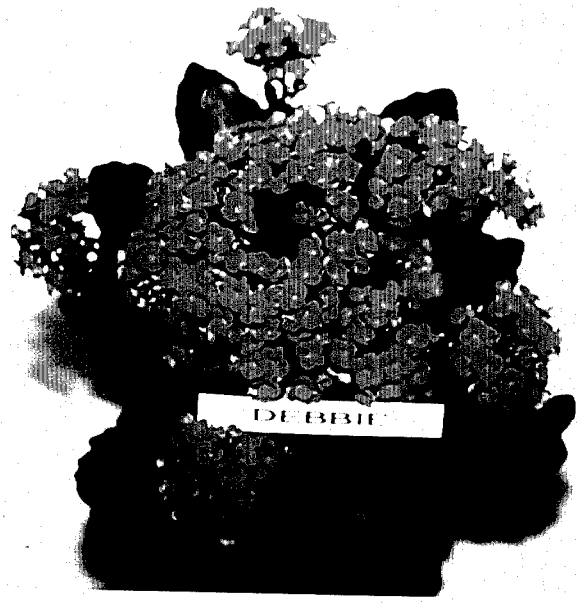
FIG. 2 is a topview of 'Debbie' showing the flowers and inflorescence in greater detail.
Figure 3:
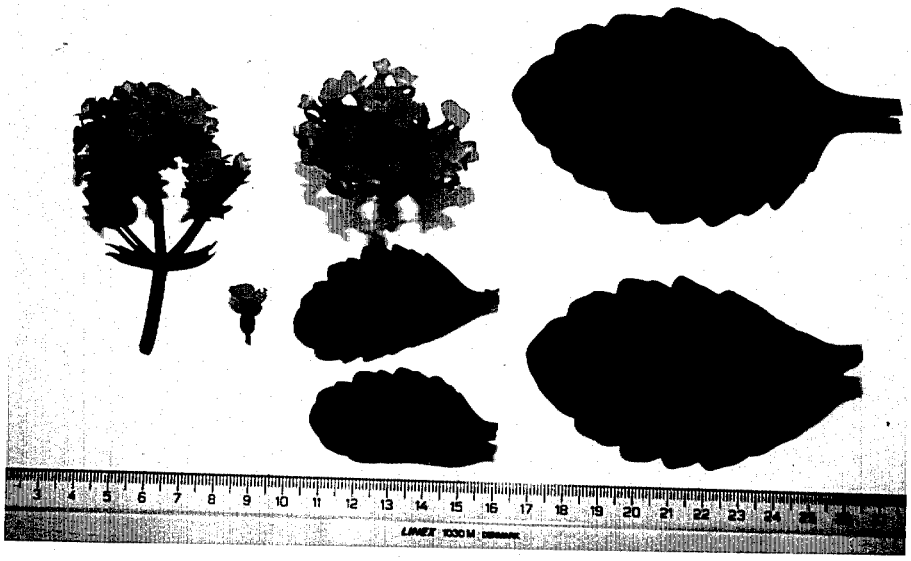
FIG. 3 is a close-up of representative flowers and leaves.

In the following description, color references are made to The Royal Horticultural Society Colour Chart (RHS), except where general colors of ordinary significance are referred to. Color values were taken under diffuse natural light conditions at approximately 12:00 a.m. in Hinnerup, Denmark.

Botanical classification:

*Commercial.*—Kalanchoë cv. 'Debbie'.

Parentage:

*Male parent.*—'Rako'.

*Female parent.*—'Janni'.

Propagation: The new cultivar holds its distinguishing characteristics through successive propagations by leaf cuttings and by division of shoots.

*Type cutting.*—Top shoot.

*Time to root.*—Ten days.

*Rooting habit.*—Branched roots produced from callus.

Plant description:

*Form.*—Compact, bushy plant with multiple flowering shoots. Height ca. 24 cm. Diameter ca. 18–20 cm.

*Habit of growth.*—Upright growth, short internodes, short and upright flowering shoots.

*Foliage description.*—Narrow and small leaves with short petioles. The leaf size is reduced when the floral stage is induced. Size: Vegetative leaf is approximately 10.7×7 cm. The leaves produced by flowering plants are approximately 7.5×4.5 cm. Shape: Oval with an obtuse leaf tip. Texture: Glabrous. Margin: Undulate. Color: Young foliage (topside): RHS 137A. (underside): RHS 138A. Mature foliage (topside): RHS 139A. (underside): RHS 137A.

Flowering description:

*Flowering habit.*—Flowering is induced by short day length. Cymes are formed.

*Natural flowering season.*—The natural flowering season is winter and spring. Flowering time under controlled day length at 20° C. in summer is 8 weeks. In winter (with artificial lighting) at 20° C. the flowering time is 9 weeks. Flowering time depends on temperature, light intensity and other growing conditions.

*Flower buds.*—Dusty red bud color. RHS 42A. Size: 1×0.3 cm just before anthesis. Shape: Narrow. Rate of Opening: 50% open 1.5 weeks after first open flower.

*Flowers borne.*—The flowers are borne in dishasial cymes developing from leaf axils. The main inflorescences are branched into one central and 2–4 minor cymes during development.

*Quantity of flowers.*—10–15 headbunches with 30–50 flowers in 15–30 secondary bunches with 10–15 flowers. (Unpinched plants).

*Petals.*—Shape: Round obovate with cuspidate leaf tips. Color: Top side when opening RHS 43A; under side 43B. Number of petals: Four (4). Size of flowers: The petals measure 0.6 cm in diameter and the total flower diameter is 1.9 cm.

*Reproductive organs.*—Stamens: Eight (8) in number. Anther Shape: Slightly oblong. Filament color: Yellow/green. Pollen color: Yellow. Pistils: Stigma: Round. Style color: White. Ovaries: Four (4) ovaries each measuring 0.5×0.1 cm. The ovaries are light green and superior (hypogonous).

Disease resistance: No known Kalanchoë diseases observed to date. Resistance not observed.

General observations: 'Debbie' produced high-quality plants without pinching when grown in 9–10 cm pots with one cutting per pot. For larger 12 cm pots high-quality plants are produced when three cuttings or one pinched cutting is used per pot.

I claim:

1. A new and distinct Kalanchoë plant named 'Debbie' as described and illustrated.

* * * * *